(12) United States Patent
Fuisz et al.

(10) Patent No.: US 11,666,475 B2
(45) Date of Patent: *Jun. 6, 2023

(54) DEVICE AND METHOD FOR REDUCING URINARY RETENTION

(71) Applicants: Joseph M. Fuisz, Nashville, TN (US); Richard C. Fuisz, Franklin, TN (US)

(72) Inventors: Joseph M. Fuisz, Nashville, TN (US); Richard C. Fuisz, Franklin, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/557,099

(22) Filed: Dec. 21, 2021

(65) Prior Publication Data

US 2022/0387210 A1    Dec. 8, 2022

Related U.S. Application Data

(63) Continuation-in-part of application No. 17/342,272, filed on Jun. 8, 2021, now Pat. No. 11,213,421.

(51) Int. Cl.
*A61F 5/453* (2006.01)
*A61F 5/44* (2006.01)

(52) U.S. Cl.
CPC ............ *A61F 5/453* (2013.01); *A61F 5/4404* (2013.01)

(58) Field of Classification Search
CPC ........ A61F 5/453; A61F 5/4404; A61F 5/451; A61B 10/007; A61G 9/00; A61G 9/003; A61G 9/006; A47K 11/04; A47K 11/06; A47K 11/08; A47K 11/12

See application file for complete search history.

(56) References Cited

U.S. PATENT DOCUMENTS

| | | | |
|---|---|---|---|
| 221,207 A | * | 11/1879 | Avery .................... B29C 33/02 198/713 |
| 651,310 A | | 6/1900 | Hogan |
| 920,463 A | | 5/1909 | Hogan |
| 1,237,483 A | | 8/1917 | Darnell |
| 1,801,030 A | | 4/1931 | Vasse |

(Continued)

OTHER PUBLICATIONS

List of thermal conductivities. www.chemeurope.com/en/encyclopedia/List_of_thermal_conductivities.html. Accessed Jul. 21, 2021.*

(Continued)

*Primary Examiner* — Adam Marcetich
(74) *Attorney, Agent, or Firm* — Fitch, Even, Tabin & Flannery, LLP

(57) ABSTRACT

A device to facilitate urination by a male includes a vessel having a contact surface area at and adjacent a top edge of the vessel configured to be placed in contact with the penis. The contact surface area includes a thermally conductive material and has a shape configured to reduce pressure requirements for urination from a standing position as compared with urinating into a toilet from a standing position. A method of reducing urinary retention in a male includes contacting the penis of the male with a contact surface area of a device, which may be as described above, and urinating while the male is in a standing position with the penis in contact with the contact surface area, wherein the contact surface area comprises a thermally conductive material and is at an initial temperature at least 14° F. lower than a temperature of the penis.

36 Claims, 6 Drawing Sheets

(56) References Cited

U.S. PATENT DOCUMENTS

| | | | | |
|---|---|---|---|---|
| 2,006,704 | A * | 7/1935 | Van Muffling | A47J 36/00 |
| | | | | 222/572 |
| 2,594,339 | A | 4/1952 | Nugent | |
| 3,479,671 | A | 11/1969 | Beich | |
| 4,665,571 | A | 5/1987 | Muccione | |
| 5,331,689 | A * | 7/1994 | Haq | A47K 11/12 |
| | | | | 604/326 |
| 5,926,858 | A | 7/1999 | Heller | |
| 6,216,909 | B1 * | 4/2001 | Lin | A47J 45/066 |
| | | | | 220/756 |
| 9,089,315 | B1 * | 7/2015 | Ahlering | A61B 18/02 |
| 2005/0066432 | A1 | 3/2005 | Gouldsworthy | |
| 2009/0105793 | A1 | 4/2009 | Brown | |
| 2011/0114648 | A1 * | 5/2011 | Proskey | B65D 81/3874 |
| | | | | 220/592.17 |
| 2013/0233866 | A1 * | 9/2013 | Dooley | A47G 19/2288 |
| | | | | 220/592.17 |
| 2013/0261419 | A1 | 10/2013 | Davidson | |
| 2014/0303584 | A1 | 10/2014 | Keating | |
| 2016/0095479 | A1 | 4/2016 | Jenkin | |
| 2018/0015649 | A1 * | 1/2018 | Hutchinson | B29C 33/02 |

OTHER PUBLICATIONS

List of thermal conductivities. https://www.chemeurope.com/en/encyclopedia/List_of_thermal_conductivities.html. Accessed Jul. 21, 2021.

Fowler, Clare J., Derek Griffiths, and William C. De Groat. "The neural control of micturition." Nature Reviews Neuroscience 9.6 (2008): 453-466. (Year: 2008).

Geirsson, Gudmundur, Sivert Lindstrom, and Magnus Fall. "The bladder cooling reflex and the use of cooling as stimulus to the lower urinary tract." The Journal of urology 162.6 (1999): 1890-1896. (Year: 1999).

Al-Hayek, Samih, and Paul Abrams. "The 50-year history of the ice water test in urology." The Journal of urology 183.5 (2010): 1686-1692. (Year: 2010).

* cited by examiner

DEVICE AND METHOD FOR REDUCING URINARY RETENTION

BACKGROUND OF THE INVENTION

Benign prostatic hyperplasia (BPH) typically begins after the age of forty, and half of males fifty and over are affected. By the age of eighty, 90% of males are affected.

Various pharmacological treatments exist, including, inter alia, alpha blockers such as tamsulosin, 5α-reductase inhibitors such as finasteride, and phosphodiesterase type 5 inhibitors, such as tadalafil. Unfortunately, pharmacological treatments are not always completely sufficient to the task.

Various surgical and non-surgical interventions are also employed, such as prostate surgery, including inter alia the use of devices like Urolift®. Urolift® is an FDA-approved implanted device placed through the obstructed urethra, and placed permanently to hold the enlarged prostate tissue out of the way and increase the opening of the urethra.

Other interventional procedures include transurethral microwave therapy (TUMT). TUMT employs a microwave antenna attached to a flexible tube that is inserted into the bladder, and microwave heat is used to kill off excess prostate tissue.

Laser surgery is also used to destroy prostate tissue and shrink the gland.

Transurethral incision of the prostate (TUIP) is another surgical solution. It involves cuts being made in the prostate to reduce the prostate's pressure on the urethra, and may be recommended for smaller prostates. One downside is the frequent need to repeat the procedure.

The most common surgery for BPH is transurethral resection of the prostate (TURP). In TURP, the physician removes portions of the prostate using a scope inserted through the urethra.

These various surgical interventions involve known side effects, some of which are serious and have adverse quality of life implications.

BPH is characterized by a spectrum of obstructive and irritative symptoms, known collectively as LUIS (lower urinary tract symptoms). Poor urinary flow and the sensation of incomplete bladder emptying are the two symptoms that correlate most closely with the eventual need for prostate surgery. Untreated, a significant number of men with BPH will eventually develop acute urinary retention.

Urinary catheters are frequently used to empty the bladder where the bladder is not voided adequately by the patient, and in some cases patients will be asked to self-administer catheters. This is obviously painful, uncomfortable, inconvenient, and demoralizing.

The demoralizing aspects of poor urine streams and sleep interruption should not be discounted as a critical quality of life issue for afflicted men.

It is noted that BPH is not the sole cause of urinary retention in men. Decreased contractility of the detrusor muscle can also make it difficult to effectively empty the bladder, and impossible to fully empty the bladder.

Known causes of urinary retention include bladder issues such as: detrusor sphincter dyssynergia, neurogenic bladder, iatrogenic scarring of the bladder, and other bladder issues Prostate related causes of urinary retention include BPH, prostate cancer, pelvic malignancies, and prostatitis.

Urinary retention is a common pre and post-operative condition that disproportionally impacts older men. Medications are available to aid in voiding but they usually do not result in the voiding of residual bladder urine.

Regardless of any invasive or non invasive surgical procedures, it is common for incomplete bladder emptying to continue with its accompanying urinary urgency and need for double voiding. Hence the invention.

A post-void residual urine of any amount is significant and increases the potential for recurring urinary tract infections stone formation and perhaps most importantly contributes to a lesser quality of life in the day and increased trip to the bathroom at night while trying to sleep. They can also interrupt day time activities.

Most people wake up once or twice during the night. Reasons this might happen include drinking caffeine or alcohol late in the day, a poor sleep environment, a sleep disorder, or another health condition, such as BPH. When a person cannot get back to sleep quickly, that person does not get enough quality sleep to keep refreshed and healthy.

Urinary retention, apart from discomfort and practical quality of life implications, also results in residual urine or urinary stasis, which can lead to an increased risk of urinary tract infection, bladder stones and other consequences such as atrophy of the detrusor muscle, atonic bladder, hypertrophy of the detrusor muscle, diverticula, hydronephrosis (congestion of the kidneys), and others.

BRIEF SUMMARY OF THE INVENTION

The present invention relates, inter alia, to a device to facilitate urination by a male, comprising a vessel having a contact surface area at and adjacent a top edge of the vessel configured to be placed in contact with the penis and/or scrotum, the vessel being capable of collecting urine, wherein the contact surface area comprises a thermally conductive material, and wherein the contact surface area has a shape configured to reduce pressure requirements for urination from a standing position as compared with urinating into a toilet from a standing position.

The thermally conductive material may have a thermal conductivity of greater than 20 watts per meter-kelvin.

The contact surface area may be at least 0.5 square inches, preferably at least 1 square inch.

The contact surface area of the vessel may slope inwardly from the top edge of the vessel toward the bottom of the vessel.

When the top edge of the vessel is horizontal, the contact surface area may be at an angle of less than 45° to vertical.

The vessel or device may have a protrusion with a contact surface area to facilitate contact with the scrotum to assist with and promote urination. In certain embodiments, the portusion extends from the side of an otherwise cylindrical vessel.

The contact surface area may have an angled, curved or concave shape to increase contact with the penis. The top edge of the vessel may have an hourglass shape comprising two wider portions forming openings separated by a narrower portion.

The contact surface area may comprise at least one material selected from the group consisting of stainless steel, steel, silver, aluminum, tin, copper, nickel, zinc, iron, magnesium and brass. Thermally conductive additives including without limitation specialty graphite fibers may be employed. Thermoconductive plastics may be used (for example and without limitation, Therma-Tech thermally conductive formulations from PolyOne). Thermoconductive ceramics may be employed.

The vessel may include markings to show volume.

The vessel may comprise an antimicrobial coating on its surfaces.

The contact surface area may comprise a thermally conductive material preferably having a thermal conductivity of at least 20 watts per meter-kelvin. At least some portions other than the contact surface area of the device may comprise a material having a thermal conductivity less than that of the contact surface area. Such embodiments may be desirable to retard the transfer of heat from urine to the contact surface area. Non limitative embodiments include a vessel with a lower portion made from a relatively non-thermoconductive material mated to an upper contact surface portion comprising a more theromconductive material. In yet another embodiment, the non-contact surface area is insulated with a less-thermoconductive coating or layer to retard heat transfer from urine during use. Generally, such coating or layer will correspond (or exceed) the urine contact surface area.

The present invention also relates to a method of reducing urinary retention in a male, comprising contacting the penis of the male with a contact surface area of a device and urinating while the male is in a standing position with the penis in contact with the contact surface area, wherein the contact surface area comprises a thermally conductive material and is at an initial temperature at least 14° F. lower than a temperature of the penis.

Embodiments of the present invention may be used in any position—not merely a standing user.

The device used in the method may be as described above and hereinafter.

The device may be used to treat urinary hesitancy in men who do not suffer from BPH; for example, the device may be used for men with male voiding dysfunction. For example, certain men suffer from poor coordination between the bladder muscle and the urethra. This may result in incomplete relaxation or over-activity of the pelvic floor muscles during voiding. Voiding symptoms represent a continuum of what is referred to as Lower Urinary Tract Symptoms (LUTS), which may be treated with embodiments of the current invention.

Embodiments of the present invention may also be used to treat pelvic floor hyperactivity, neuro-sensory dysregulation within the bladder which can be reflected as sensory instability, inappropriate bladder contractions, bladder hyperreflexia, poor bladder compliance, or neuro-sensory dysregulation. Treatment with the device may assist in succession urination, including as self-reported by patient-users as compared with a control group.

Embodiments of the present invention may be used to treat overactive bladder. Embodiments of the present invention may be used to treat neurogenic detrusor overactivity.

Use of embodiments of the present invention may be used to reduce scores on the International Prostatism Symptom Score (IPSS) test as compared with non-users or users of a control. IPSS refers to the International Prostate Symptom Score. The IPSS may be reduced by 2 or more points, preferably by 3 or more points, most preferably by 5 or more points, as compared with a control group.

Embodiments of the present invention may be used to reduce nocturia, as compared with non-users or users of a control. Preferably nocturia are reduced (per sleep cycle) by 0.5 times or more, more preferably by 1 time or more, still more preferably by 2 times or more.

Embodiments of the present invention may be used to increase average total sleeping time, by reducing nocturia and/or otherwise extending time between nighttime voids. Users may increase their average total sleep time (as compared with a control group) by at least five minutes, preferably by at least ten minutes, more preferably by least fifteen minutes, most preferably by at least twenty minutes.

Embodiments of the present invention may be used to increase average total rem sleeping time, by reducing nocturia and/or otherwise extending time between nighttime voids. Users may increase their average total REM sleep time (as compared with a control group) by at least five minutes, preferably by at least ten minutes, more preferably by least fifteen minutes, most preferably by at least twenty minutes.

Embodiments of the present invention may be used to reduce the number of small urinary evacuations (defined here as urinations under 50 ml volume) as compared with non-users or users of a control. Preferably, small urinary events are reduced by at least 0.5 per day, preferably by at least 1 per day, more preferably by at least 1.5 per day.

Embodiments of the present invention may be used to extend the longest duration between urinations for a group of users, as compared with a control group of non users (measured as the longest duration between voids during a day, such longest void times added and divided by the number of days to reach an average). Embodiments of the present invention may extend the average longest duration between urination by at least fifteen minutes, preferably by at least thirty minutes, more preferably by at least forty-five minutes.

The method may further comprise treating the male with a drug therapy, including without limitation a drug therapy selected from the group of alpha blockers, 5α-reductase inhibitors and phosphodiesterase type 5 inhibitors. The method may further comprise treating the male with drug therapy for overactive bladder syndrome.

The method may further comprise at least one additional urination prior to urinating while the male is in a standing position with the penis in contact with the contact surface area, wherein a void interval between urinations is less than twenty minutes, less than fifteen minutes, less than ten minutes or less than five minutes.

Embodiments of the present invention may be used to reduce the time to double void, by making it easier for the user to initiate a double void. The invention, as compared with a control group, may permit a group of patients to double void within shorter intervals than the control group. The average double void time may be 10% faster, preferably 20% faster, most preferably 30% faster, on average, than the control group.

Embodiments of the present invention may be used to facilitate increased use of double voids by making it easier to initiate such double voids. Embodiments of the present invention may be used to increase the number of double voids (defined as a second void within twenty minutes of the preceding void) by users. As compared with a control group, users may increase their double void activity by at least one double void per day, preferably by at least two double voids per day, more preferably by at least 2.5 double voids per day.

Embodiments of the present invention may be used to reduce urinary dribbling as compared with a control group of non-users or placebo. Dribbling is a significant quality of life issue. As compared with a control group of non-users, use of embodiments of the present invention may statistically reduce the occurrence of dribbling episodes, by 1 or more times per week, preferably by 3 or more times per week, more preferably by 5 or more times per week.

Reduction of incontinence episodes in patients with overactive bladder syndrome may be more dramatic. Embodiments of the device may reduce the number of daily incontinence episodes by 0.5 per day, preferably, 1 per day, more preferably 1.25 per day, most preferably 1.5 per day. These results are comparable to the efficacy of Myrbetriq®.

The device may be co-administered, used or prescribed in conjunction with drugs uses to treat overactive bladder syndrome.

The method may further comprise at least one additional urination prior to urinating while the male is in a standing position with the penis in contact with the contact surface area, wherein a void interval between urinations is less than ten minutes, and the retained urine in the bladder is reduced at least 20% for a given patient population (as compared to a control group urinating in a standing position into a toilet or wall urinal, or other control conditions).

DETAILED DESCRIPTION OF THE INVENTION

Figure 1:
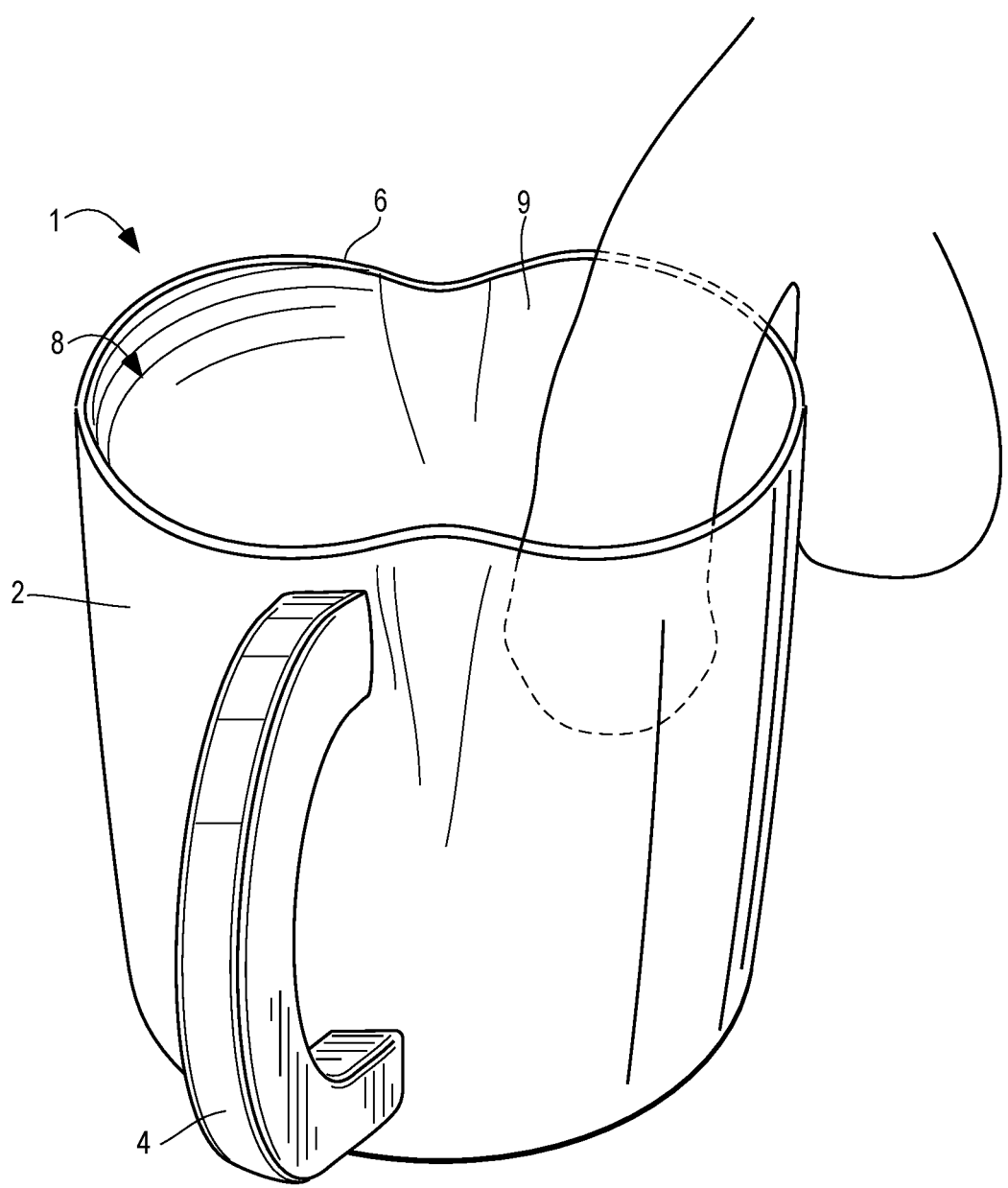
FIG. 1 is a perspective view of an embodiment of the device of the present invention, with penis inserted, using an hourglass (or figure-eight shape) for the vessel for maximal skin exposure.

One embodiment of the invention is a vessel made of a high thermal transfer material, in which is placed the penis of a standing man, preferably with the device touching directly or indirectly the scrotum, transfers heat from the body to the vessel, and assists in passing urine and reducing retention of urine in the bladder. This transfer involves the loss of penile (and/or scrotum) heat (perceived coldness) to the vessel. The device is not intended by itself to be a treatment for BPH but is meant as a key adjunct to medication and surgical type procedures. While the physiological reason for the device assisting in passing urine and reducing retention of urine in the bladder is not completely known, it is postulated that, the device assists in passing urine and reducing retention of urine in the bladder because of thermal conductivity (described hereinafter) and because the pressure of a standing male, whose penis is directed downwards in its natural position, avoids kinks in the urethra when voiding which might otherwise be caused by the growing inelasticity of the male's urethra with aging. In addition, the use of the device reduces pressure required to propel urine on a forward trajectory to a toilet or urinal.

In adults older than 50 years, 30-100 ml or more of residual urine may remain after each voiding because of the decreased contractility of the detrusor muscle or lack of sufficient pressure to expel urine into the toilet bowl. There may be a lack of a stimulus to release the urinary sphincter musculature. In retention, ultrasound of the bladder may show increase in bladder residual urine.

The present invention relates to a non-invasive device that can be used to reduce or effectively eliminate urine retention; we call this device the virtual catheter. The virtual catheter is a vessel used to collect urine, typically from a standing male (though the virtual catheter may be used from non-standing positions)

The virtual catheter device, described herein, provides thermal transfer, reduced pressure and unknown neurogenic based stimulus to release the urinary sphincter and initiate and continue urination, and help the user of the virtual catheter to more fully evacuate the bladder of urine.

By placing the penis into the high thermal transfer vessel, made of, e.g., metal such as stainless steel, shaped as to maximize contact with penile skin and ideally, also directly or indirectly holding the device against the scrotum, preferably while the man is standing, which increases gravitational pressure and reduces pressure needed to push urine forward to a toilet, it becomes far easier to release the sphincter and void into the vessel and more completely empty the bladder. In terms of temperature, the vessel may be at room temperature let us say 70 degrees F. and the penile and scrotal skin may be at body temperature of approximately 98.6° F. or slightly lower. This effect in the standing position with accompanying increased pressure, causes more complete voiding (though not requiring the pressure required to direct urine to a conventional toilet). The inventors are not aware of this temperature effect ever being used in a method or device for passing urine and/or reducing retention of urine in the bladder. However, an urge to urinate may be experienced by men with BPH when coming inside from a zone of different temperature, such as coming into a warm building from the cold. The neurogenic reason for the temperature effect is not determinable.

The device may feature a contact area for the scrotum, typically a protrusion or raised area that rises away from the shape of the vessel. The contact area is typically a discreet protrusion, rather than a protrusion that goes all the way around the vessel, so as to avoid interference with the handle. However, it is possible to have a protrusion that goes all the way around the vessel that does not interfere with the handle. The protrusion has a contact surface area that typically will have identical or comparable thermoconductive properties as the contact surface area for the penis itself. The protrusion allows for an ergonomic fit wherein the scrotum is contacted.

While it is expressly contemplated that the vessel can be used for non-BPH patient populations, it is generally desirable that the vessel be of a suitable weight for an older person to comfortably hold. Preferably, the dry weight of the vessel is less than 750 grams, preferably less than 650 grams, more preferably less than 550 grams, and most preferably less than 500 grams. These mass ranges are not limitative.

Now this non-intrusive device allows for the more complete passage of urine, more complete emptying of the bladder even after a user's double urinary void in the toilet (see testing results discussed below). This is especially useful at night after the double void but is also useful in the daytime after a single void in the toilet and again as can be seen in a test subject. It increases the time interval wherein the urge to void returns. In certain embodiments, in increases the time between voids by many minutes. Average times between voids for a given group (measured as average time between voids, excluding double voids) may be increased by seven minutes or more, preferably ten minutes or more, more preferably 12 minutes or more, most preferably 18 minutes or more as compared with a control group. The average void times may be measured on a 24 hour cycle, or measured during the day or non-sleeping cycles.

In addition, it has been found that it can reduce the time interval between the first and second void, (IBD) by use of the vessel described for the second void.

It is a purpose of the virtual catheter device to facilitate urination using thermal conductivity—using a temperature stimulus—on the penis and optionally the scrotum, directly or indirectly, as well as reducing required pressure since the patient is standing and the penis is pointing downward in its usual position therefore avoiding any kinking of the urethra in the older individual with less tissue elasticity A device may be made that creates the thermoconductive effect of the present invention but is easy to use when the user is seated on the toilet. Such a device may comprise a contact surface for the penis and/or scrotum but not be a vessel for receiving or collecting urine, since it may be difficult to maneuver the vessel into place for a user seated on toilet. In such a configuration, the device may be a manageable stick-like device with contact surface area for the penis and or/scrotum that can be comfortable contacted with the penis in a non-standing position, for example a user on the toilet.

There is a need for a non-invasive treatment to reduce urinary retention.

It is an object of certain embodiments of the present invention to assist a patient in more consistently evacuating the bladder, i.e., substantially reducing or eliminating retained urine in the bladder. Retained urine volume may be, for a given urination protocol, may be reduced at least 10%, preferably at least 20%, more preferably at least 30%, most preferably at least 40% for a given patient population as compared with a control group. Retained urine may be measured after voiding, after double voiding, or measured using random or set test protocols.

It is an object of certain embodiments of the present invention to extend or prolong sleeping intervals for patients that are otherwise awoken by urinary urgency, including inter alia users who suffer with BPH.

Shortening double or triple void times can make it easier for patients to fall back asleep by reducing the period of time between voids during which time a patient may become distracted, become fully awake, and have a harder time falling back asleep. This reduces their total sleep time. Such periods of being awake may also reduce the activity of antidiuretic hormone (ADH).

Improvement in sleep—whether total sleep, interrupted sleep intervals, increases in REM sleep—can all significantly improve quality of life for patients with urinary issues.

Normally, the amount of ADH in the body is higher during the night. This helps prevent urination while you are sleeping. But if the levels of ADH remain low during the night, the body will produce large amounts of urine, so urination during the night is more likely. Hence the importance of the reduced DVI so as to not reduce ADH formation.

It is an object of certain embodiments of the present invention to reduce the risk (and frequency) of urinary tract infections (UTI). It is an object of embodiments of the present invention to reduce the prevalence of UTI in adult males (including adult males with BPH) by at least 15%, preferably by at least 20%, most preferably by at least 25%, as compared with a similarly aged, healthy control group.

It is an object of certain embodiments of the present invention to reduce urinary tract infections, in incidence and/or severity, on a statistically significant level.

It is an object of certain embodiments of the present invention to reduce or eliminate the formation of bladder stones, through a modality of reducing or eliminating retained urine. It is an object of certain embodiments of the present invention to reduce the incidence of bladder calculi in men with BPH by at least 2.5%, preferably by at least 10%, most preferably by at least 20%, as compared with a similarly aged (or otherwise appropriately batched), control group not using the virtual catheter.

It is an object of certain embodiments of the present invention to reduce or eliminate the need for conventional catheter placement after certain urological procedures, increasing patient comfort, decreasing the need for follow on medical care, and reducing the risk of scarring and other tissue damage for urethral catheter insertion.

It is an object of certain embodiments of the present invention to employ the virtual catheter as a diagnostic device to ascertain retained urine after conventional urination (potentially replacing the need for ultrasound or other imaging to determine retained urine after the patient pees).

It is an object of certain embodiments of the present invention to allow a user of the virtual catheter to track urine collection over time.

It is an object of the invention to reduce the time interval between double voiding, the double voiding interval (DVI). Double voiding is almost universally recommended in all patients with BPH.

In certain embodiments, the virtual catheter is prescribed for a patient in conjunction with a pharmaceutical agent, including without limitation, one or more of: alpha blockers such as tamsulosin, 5α-reductase inhibitors such as finasteride, and phosphodiesterase type 5 inhibitors, such as tadalafil. The virtual catheter may be prescribed or used with other drug therapies, and or device therapies. In certain embodiments, the virtual catheter is prescribed together with one or more of the above-reference drugs, optionally as a drug-device combination.

Embodiments of the present invention promote more complete urinary flow and prevent dribbling.

Embodiments of the present invention comprise a non-invasive device that is placed in contact with the penis prior to, and during, urination.

Typically, the user's urine is collected in the device, and then emptied by the user.

Typically, the device is used by a standing user, but it is possible to use the device in a non-standing position. The ability to stand using the virtual catheter is a significant advantage; many older males find it uncomfortable to repeatedly sit and stand from the toilet, particularly in view of their frequent urination patterns.

Embodiments of the present invention comprise a cup or vessel. Optionally, the outer margin is ergonomically designed to increase surface area contact between the upper edge of the cup shaped device and the penis. Optionally, the upper, inner portion is ergonomically designed to increase surface area contact between the upper, inner portion of the cup shaped device and the penis.

Two mechanisms are employed, which are both novel to the literature and medical practice.

The first mechanism is the use of a temperature differential as a stimulus. The second mechanism is in the reduction of required pressure. The combination of these two mechanisms provides improved results.

In embodiments of the present invention, the penis is placed against a material that is lower in temperature surface body temperature (here, temperature of the penis). This temperature differential is preferably at least 15° F., preferably at least 20° F., more preferably at least 25° F., and most preferably at least 35° F.

Normal temperature of a flaccid penis is 91.7° F. to 92.8° F., as reported in the literature. Thus, a cup shaped device at ambient temperature of 75° F. will have a temperature differential with the penis of approximately 17° F. Now, according to Vivint.com, the average ambient temperature of a home is 68 to 76 degrees (https://www.vivint.com/resources/article/best-home-room-temperature—link retrieved on Jun. 7, 2021). The result is that ambient temperature in a home will tend to generate a significant temperature differential.

Preferably, the temperature differential is 15-40° F., preferably 25-35° F.

Rarely, it may be advantageous to chill the virtual catheter to temperatures below ambient temperatures. In such cases where the virtual catheter is chilled, a larger temperature differential will be achieved, i.e., a temperature differential of greater than 40° F.

In certain embodiments, the virtual catheter is sold, supplied, marketed, and/or approved for sale in conjunction with a cooler or refrigerator unit. Such unit may further charge the virtual catheter where the virtual catheter has a battery, Cooling and refrigeration may be combined with a cleaning system as part of the same or different units.

In certain embodiments, some or all of the material comprising the contact surface with the penis (and/or scrotum), are selected for thermal conductive properties. Generally, the higher the thermal conductive properties, the greater the effect of the temperature differential on promoting urinary flow.

Preferably, the contact surface area is comprised in part, substantially or entirely, of a material with a high thermal conductivity, measured in watts per meter-kelvin, of greater than 20, preferably greater than 100, more preferably greater than 200, and most preferably greater than 300 watts per meter-kelvin.

A preferred thermal conductivity range for the contact surface area is 20 to 500 watts per meter-kelvin.

Generally, the contact surface area must be adequate to provide a sufficient temperature-based stimulus.

In certain embodiments, the contact surface area between the vessel and the penis is at least 0.5 inch$^2$, preferably at least 0.75 inch$^2$, more preferable at least 1 inch$^2$, and most preferably at least 1.25 inch$^2$, measured as an average for a typical group of users (which may be general users or a specific sup-population of users).

In certain embodiments, the contact surface area between the vessel and the scrotum is at least 0.25 inch$^2$, preferably at least 0.5 inch$^2$, more preferable at least 0.8 inch$^2$, and most preferably at least 1 inch$^2$, measured as an average for a typical group of users (which may be general users or a specific sup-population of users).

In other embodiments, the internal wall of the virtual catheter will be sloped inwards to accommodate contact area between member and receptable wall, i.e. the penis is supported on the inward-sloping surface. Preferably, substantially all or all of the contact surface area is a high thermally conductive material.

In other embodiments, the virtual catheter will comprise a short ramp portion, akin to a ski jump, to accommodate the member and provide additional contact surface area. The ski jump is angled downwards from the plane of the top of the virtual catheter, in most embodiments. Generally, it is desirable that the "ski jump" be short enough for the tip of the penis to extend past it. The "ski jump" may be concave in shape to facilitate additional contact surface between penis and the "ski jump".

Concave, curved, or angled shapes to promote contact surface area may be employed in various designs. The vessel may use a tighter curve to increase contact surface area; a figure eight shape may be useful to have two ends with a tighter curve than would be the case for a comparably sized cylindrical design. and the handle convenient for a right or left handed person.

The geometry of the virtual catheter is important. As a receptable, the virtual catheter has a receptable function and typically will take the general form of a cup. It is not necessary for the virtual catheter to take the form of a cup, as the essential functionality is delineated above as a function of temperature stimulation and reducing pressure requirements.

The virtual catheter may channel urine into a toilet or other proper sewer, e.g., by means of a tube extending from the bottom of the vessel; it may use a separate disposable collection depot like a conventional catheter bag, provided that the virtual catheter has the ability to provide temperature stimulation to the penis and or scrotum, and reduce pressure requirements. It is conceivable that the device and method of the invention can use a tube having thermal conductive properties configured to be placed around the shaft of the penis during urination. Nonetheless, a cup like shape is the preferred embodiment.

In preferred embodiments, the weight of the virtual catheter should be comfortable to hold. Typically, the virtual catheter will have at least one external handle. The virtual catheter may have more than one external handle, for example and without limitation, two handles.

The virtual catheter is intended for use when the patient is standing, but may be used in other positions.

In certain embodiments, the vessel may be comprised of different materials or difference surfaces. As a non-limitative, example, the vessel may have a contact surface area made from stainless steel and the rest (or other parts) of the vessel may be made from a plastic.

The interior of the vessel have be made from, or have a coating or other application of relatively insulative material to prevent urine from warming the contact surface area(s) during use.

Recovery of the temperature differential between the virtual catheter and body temperature must be considered. The use of a urine-contact area with low thermal transfer properties can speed recovery. By urine contact area, we mean the portion of the vessel in contact with urine after urination into the vessel (i.e. where the urine tends to flow into the vessel—the bottom portion), understanding that there may be incidental deposit of urine on the intended contact surface area for the penis.

Preferably, the urine-contact area surface has a thermal conductivity of less than 5 watts per meter-kelvin, preferably less than 1, more preferably less than 0.5, and most preferably less than 0.3 watts per meter-kelvin.

The interior of the cup device may be scored or otherwise marked to show volume of collected urine. The exterior of the cup may be scored or otherwise marked or designed to show volume of collected urine, particularly where the cup has a transparency to see the internal amount.

In certain embodiments, the device has a white interior in whole or in part (e.g., on the bottom) to facilitate colorometric analysis of the urine.

In certain embodiments, the device may be clear or transparent in whole or in part (e.g., on the bottom) to facilitate colorometric analysis of the urine. The device may comprise a light source to facilitate colorometric analysis.

In certain embodiments, the vessel is treated in whole, in part, or substantially with an anti-microbial coating, it being noted that it is important not to adversely affect the thermal conductive properties of the contact area in preferred embodiments.

As an alternative to coatings, materials may be employed which themselves have antimicrobial, anti-bacterial, or anti-fungal activity, e.g. (and without limitation) copper or silver.

In certain embodiments, the virtual catheter device may comprise a sensor to measure urine collected. The device may comprise a clock or timer to record the time of urine collections.

The device may comprise a dissolved solids meter. The device may comprise a thermistor or temperature sensor. The device may contain optical sensors, or other sensors to determine the value of an analyte. The device may contain a camera. The cup device may have wifi, Bluetooth, cellular, or other connectivity. The device may be capable of using connectivity to convey the time, duration, amount, flow rate, flow rate duration (and commencement and conclusion), temperature, dissolved solids, analyte levels, analyte measurements or other collected information to a database. Such a database may be in the cloud, on a computer, a phone or app. The database may be accessible by a patient, caregiver, physician, or other medical professional, and may be subject to pre-set alerts. Particularly as it relates to alerts, the contents of the present applicant's U.S. Pat. No. 7,824,612 are hereby incorporated by reference herein as if fully set forth herein. Such features may be particularly useful to monitor patients post urology procedures including surgical procedures.

In certain embodiments, the device may receive or otherwise be intended and/or designed to work with reagent sticks or strips (or other reagent embodiments) for diagnostic purposes.

In certain embodiments, the device may have a high thermal conductivity neck (and/or scrotum contact surface area) with an accordion like bottom so that it is more portable for travel.

In certain embodiments, the device has a vibratory feature for additional stimulus. The vibratory feature may be turned on using a button, or automatically be triggered by a light sensor, motion sensor, liquid sensor, or other sensor. Optionally, the device comprises a power source, such as a battery.

The virtual catheter may be supplied as part of a kit with specific cleaning materials and procedures. The virtual catheter may alternatively be supplied with a cleansing device that is capable of adequately cleaning and/or sterilizing the device. Cleansing methods may include the use of temperature, cleaning agents, and ultraviolet or other light wavelengths.

It is advantageous that the urinary virtual catheter be readily identifiable for its intended use, and not readily confusable with other items. Markings, indicia, and colors may be used for this purpose.

It is important to note that urine is normally free of bacterial contamination. In certain instances, in emergency situations, it has been recommended to clean a wound with one's own urine.

In certain embodiments, the virtual catheter is a disposable, single use device. Typically, the single use version will have a metal rim, with a paper or plastic lower collection portion. However, the disposable unit may be all metal or all thermoconductive material. Optionally, the single use device folds like an accordion, or otherwise can be folded or compacted for ease of portability before use.

FIG. 1 is a perspective view of one embodiment of the device of the present invention, with penis inserted, using a figure-eight shape for the vessel. The device 1 of this embodiment includes a vessel 2 having a handle 4. An upper lip or edge 6 of the vessel 2 forms an opening 8. The upper lip or edge 6 of the vessel 2 forming the opening 8 (and cross-sectional shapes of the vessel 2 for at least a portion of the vessel adjacent the top edge 6, in planes substantially parallel to an upper lip/opening 6) may have, as shown in FIG. 1, an hourglass (or figure eight-like shape), i.e., two wider portions separated by a narrower portion. It is preferable but not required for the device 1 to include a handle 4. This shape allows for holding and use of the device by a right or left handed person.

The hourglass (or figure eight-like shape), or other concave, curved, or angled shapes promote greater contact surface area with the penis. The vessel 2 or at least the portion extending downward from the upper lip or edge 6 may use a tighter curve than that shown in FIG. 1 to increase contact surface area; a figure eight shape may be useful to have two ends with a tighter curve than would be the case for a comparably sized cylindrical design.

The internal wall 9 of the virtual catheter may be sloped inwardly from a top edge of the vessel to accommodate contact area between the penis and the receptable wall, i.e., it is configured for the penis to be supported on the inward-sloping surface. Preferably, substantially all or all of the contact surface area (area configured to be in contact with the penis and optionally the scrotum) or optionally all of the device 1 is made of or coated with a high thermally conductive material. Metals such as stainless steel, steel, silver, aluminum, tin, copper, nickel, tin, zinc, iron, magnesium (or its alloys or compounds), and brass are non-limitative examples of materials that may be employed for at least the contact surface area.

Figure 2A:
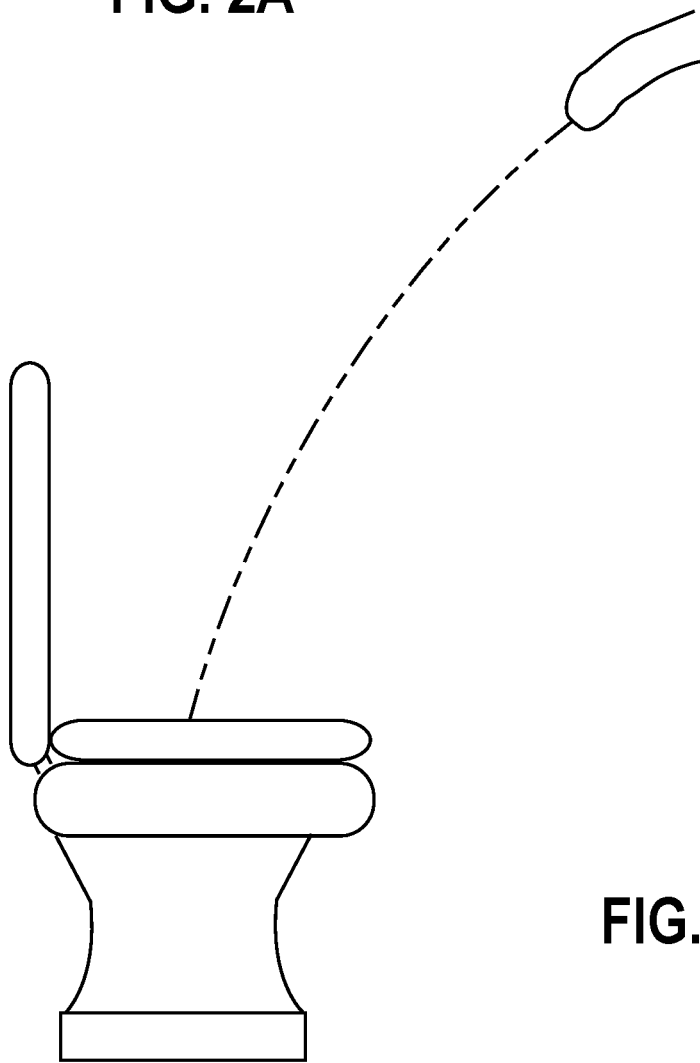
FIGS. 2A and 2B contrast the urine stream pressure required to reach a toilet from standing position (FIG. 2A) and the pressure required to urinate in the device of the present invention (FIG. 2B).
Figure 2B:
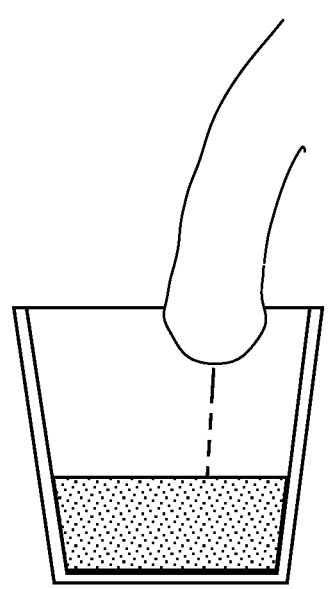

FIGS. 2A and 2B contrast the urine stream pressure illustrated with broken lines (and angle of the penis with respect to the vertical) required to reach a toilet from standing position (FIG. 2A) and the urine stream pressure illustrated with broken lines (and angle of the penis with respect to the vertical) required to urinate in the device of the present invention (FIG. 2B). As can be seen, the device can reduce the pressure necessary to expel urine as compared to reaching a toilet from standing position.

Figure 3:
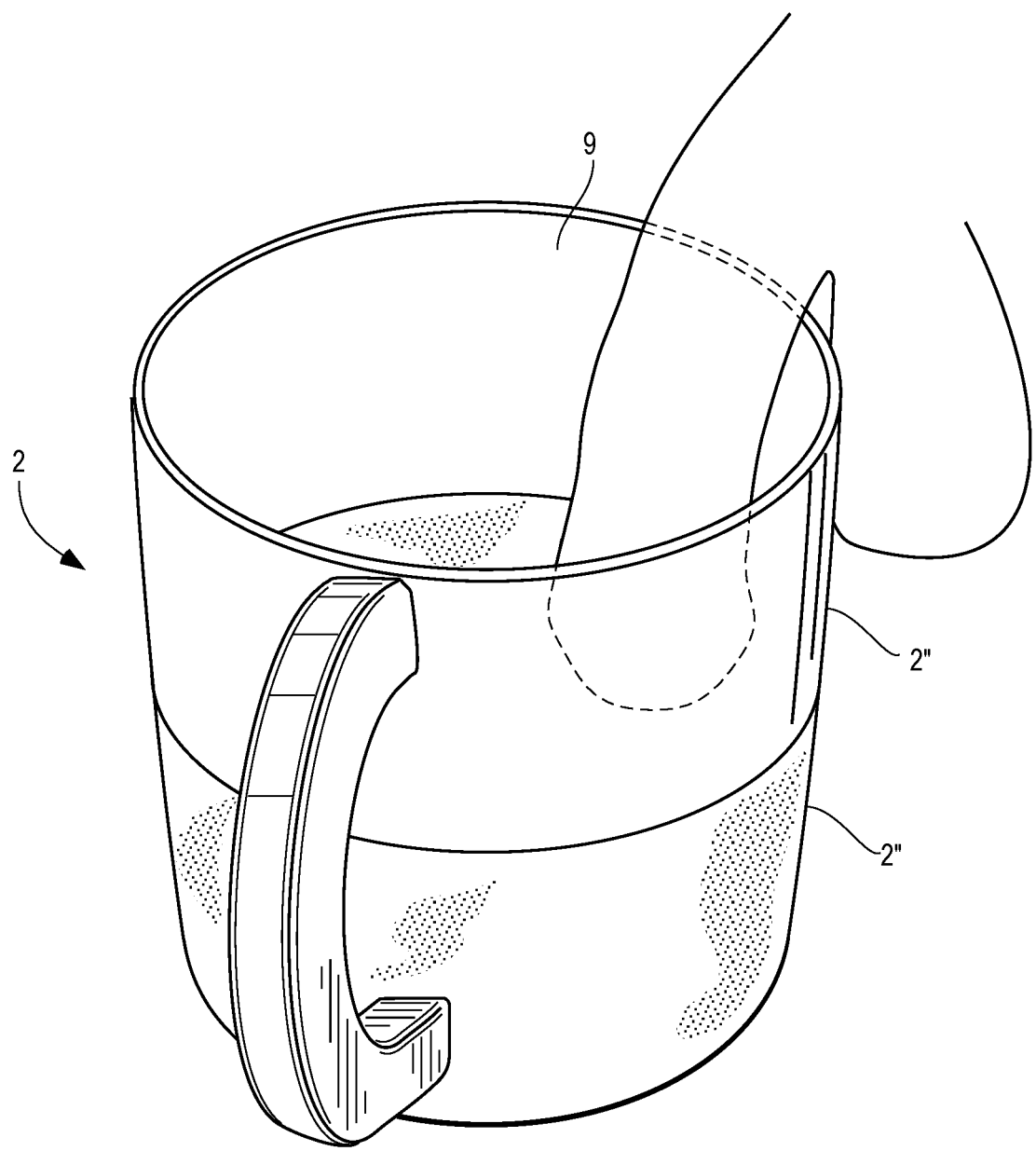
FIG. 3 is a device that is made from two distinct materials.

In certain embodiments, the vessel 2 may be comprised of different materials or different surfaces. As a non-limitative example, as shown in FIG. 3, the vessel 2 may have a contact surface area 2 inches sq made from a material with high thermal conductivity such as stainless steel and the non-contact portions 2" of the vessel may be made from less thermally conductive material such as plastic. Preferably, the contact surface area 2' has a high thermal conductivity, measured in watts per meter-kelvin, of greater than 20, preferably greater than 100, more preferably greater than 200, and most preferably greater than 300 watts per meter-kelvin.

The non-contact portion 2" of the vessel has a low thermal conductivity, measured in watts per meter-kelvin, of less than 20, preferably less than 10, more preferably less than 2, and most preferably less than 1 watt per meter-kelvin. Many plastics have a thermo-conductivity of less than 1 watt per meter-kelvin.

All thermal conductivity coefficients described herein area measured at 20 C and 1 bar.

Figure 4:
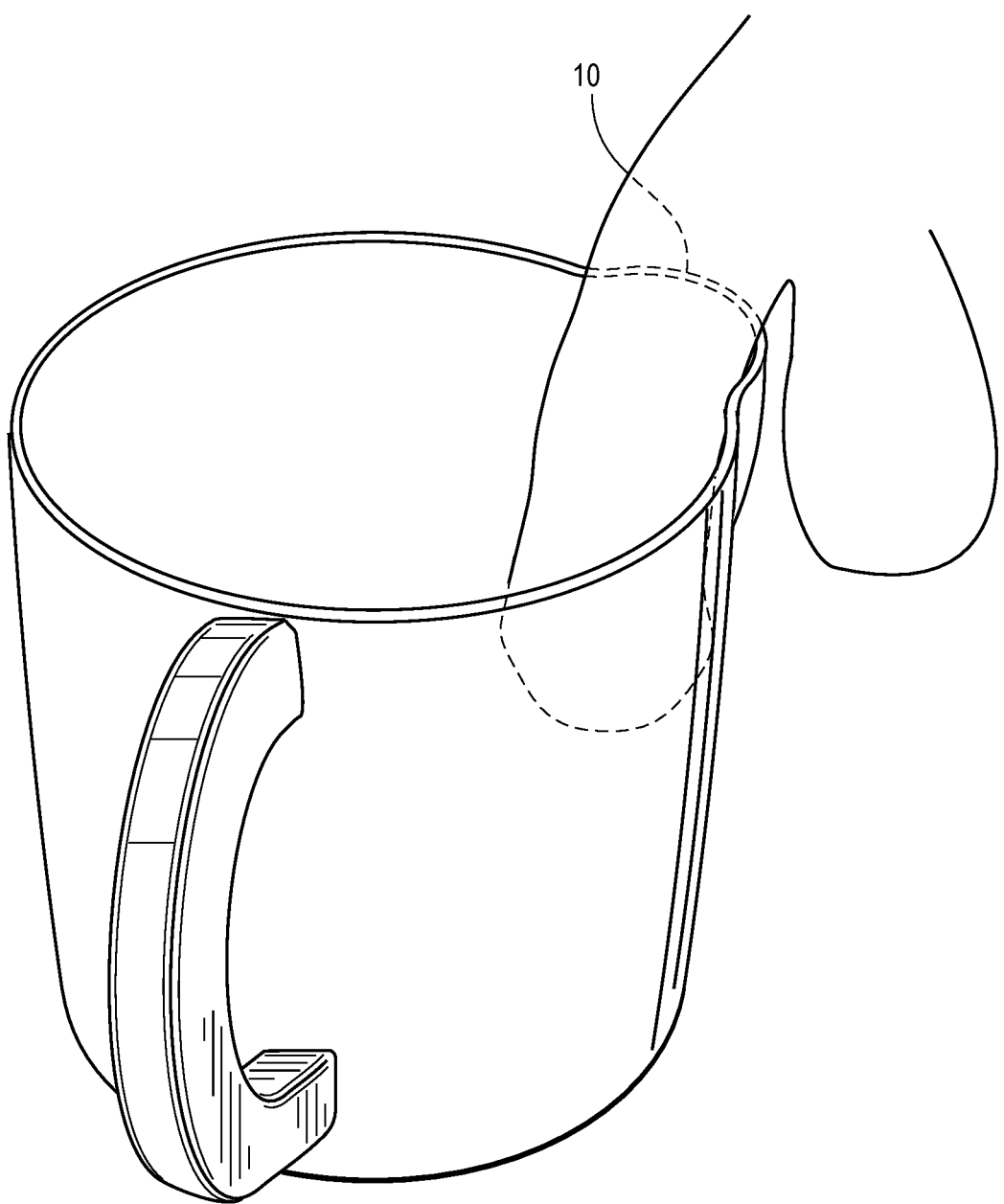
FIG. 4 is a device with a curved area to increase surface contact with the penis.

FIG. 4 shows a device with a curved area 10 having a radius of curvature similar to a radius of curvature of a flaccid penis configured to increase surface contact with the penis.

Figure 5:
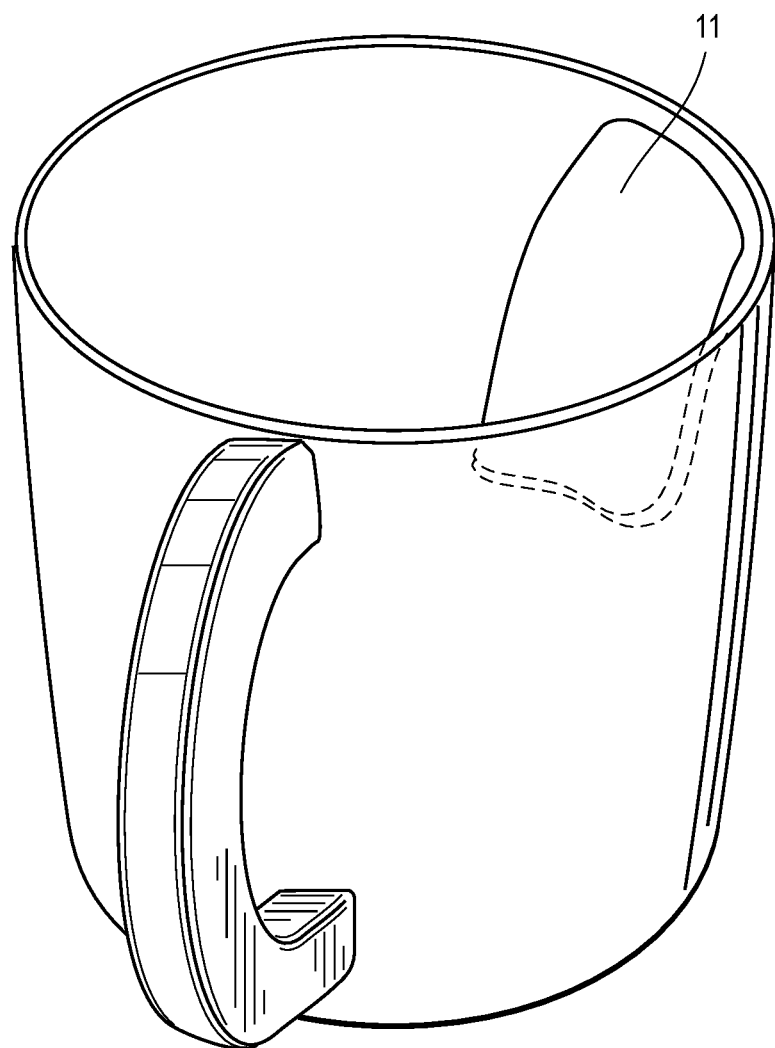
FIG. 5 has a "ski slope" feature to increase surface contact area with the penis.

FIG. 5 shows an embodiment having a sloped portion 11 or "ski slope" feature configured to increase surface contact area with the penis.

Figure 6:
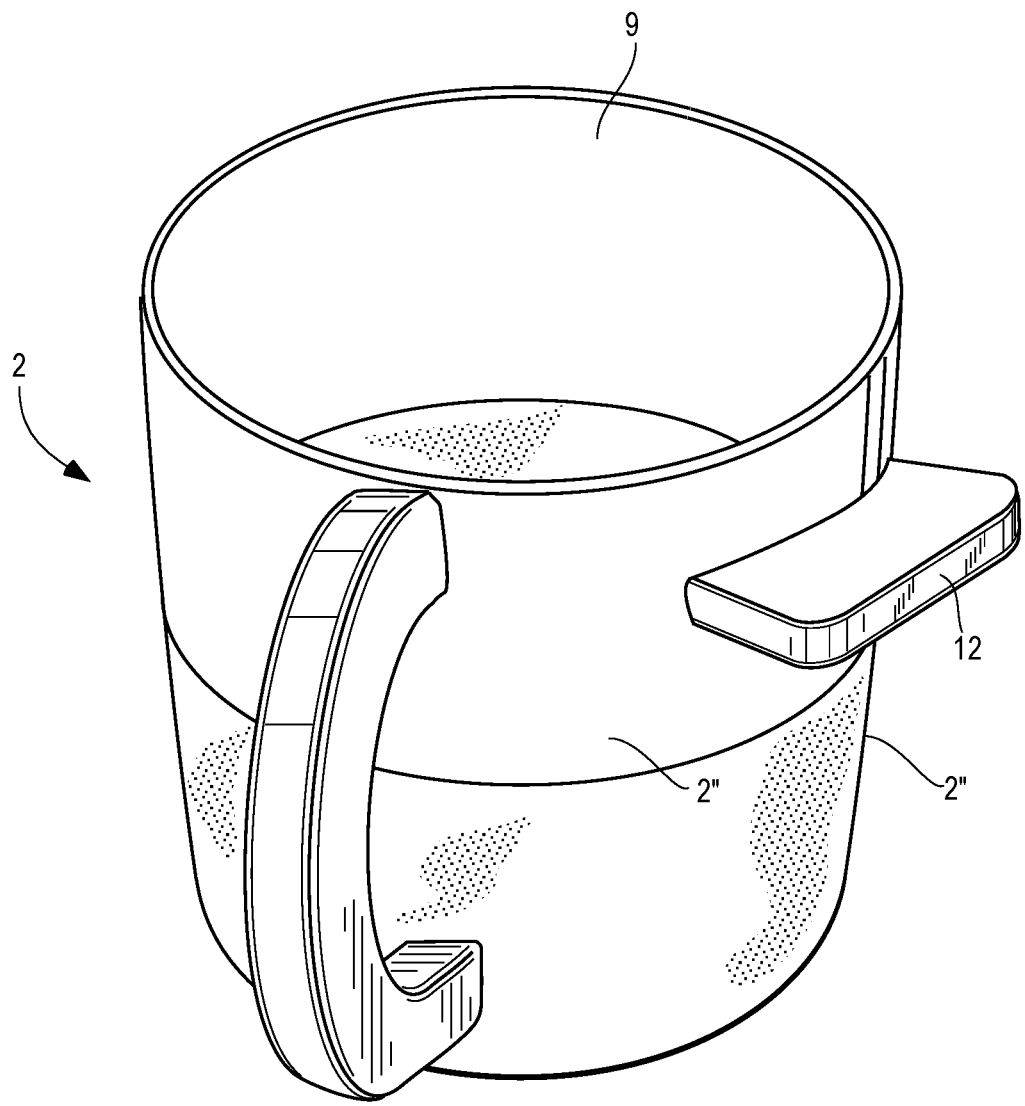
FIG. 6 has a protrusion to promote contact with the scrotum.

FIG. 6 shows an embodiment having a protrusion 12 extending outwardly from an outer wall of the vessel configured to promote and increase contact area with the scrotum.

In certain embodiments, the internal wall 9 of the vessel 2 (or the curved area 10 or sloped portion 11) on which the penis rests is sloped inwardly from a top edge of the vessel 2 toward the bottom such that, when the upper edge 6 and bottom surface of the vessel 2 is horizontal, the internal wall 9 of the vessel 2 (or the curved area 10 or sloped portion 11) is not vertical but is at a downward angle of less than 45°, more preferably less than 35°, even more preferably less that 30° to vertical. By inward angle slope, we mean the slope measured from the top of the vertical axis at the side of the vessel, inwards. The embodiment of FIG. 2B has a very modest inward slope, substantially less than 30 degrees.

As noted infra, an inward slope may be a straight angle, but it may also be a generally sloped surface that is curved or otherwise angled or not shaped as a pure slope (see, e.g., FIG. 4).

In certain embodiments, the vessel can have an opening or openable drain near or in a bottom surface of the vessel to drain the urine from the vessel. The drain may further connect to a tube, or a secondary collection chamber, or other suitable receiving area for the urine.

It is contemplated that embodiments of the present invention may be used with various double and triple void techniques.

A non-limitative series of triple urinary iterations are contemplated including inter alia: (i) toilet, toilet, vessel; (ii) toilet, vessel, vessel; (iii) vessel, vessel, vessel. A non-preferred sequence is (iv) vessel, vessel, toilet, or (v) vessel, toilet, toilet. These triple urinary sequences are preferably completed within a total of fifteen minutes, preferably within ten minutes, more preferably within seven minutes.

A non-limitative series of double urinary iterations are contemplated including inter alia: (i) toilet, vessel; and (ii) vessel, vessel. A non-preferred sequence is vessel, toilet. These double urinary sequences are preferable completed within a total of twelve minutes, preferably within ten minutes, more preferably within five minutes, and most preferably within three minutes.

The void interval is the time between voids. In the case of a double void, preferably, the void interval is less than ten minutes, preferably less than five minutes, and most preferably less than three minutes. The use of the vessel of the current invention allows for such brief effective void intervals, with substantial urine expulsion and minimizing retained urine.

The short duration of the complete sequences is particularly desirable to facilitate sleep, or to permit uninterrupted time during the day.

Embodiments of the present invention may be adapted for use by females.

Example A

This experiment will have 3 cups: one plastic (low thermal conductivity); one stainless steel (moderate thermal conductivity); and one copper (high thermal conductivity).

A ETEKCITY model 774 infrared thermometer was used in this experiment.

The cups were stored at room temperature ambient conditions and a temperature reading of each cup was taken with the following results: Plastic-72 F; Stainless Steel-72 F; and Copper-72 F Next, a finger of an adult male was measured (as proxy for the penis) and showed a temperature of 92 F Then, the finger was placed in the inside of each cup, and the adult male's temperature impression was recorded: (i) finger placed on inside of Plastic Cup . . . no distinct temperature feeling; (ii) finger placed on inside of Stainless Steel Cup distinct feeling of coolness; (3) finger placed on inside of Copper Cup . . . distinct and heightened feeling of cool/cold.

The conclusion of this experiment is that thermal conductivity is related to temperature perception/nervous system response.

Example B

In this example, an approximately 80-year old male, with BPH, volunteered to use a stainless steel vessel and a copper vessel supplied to him, and record his results. By "use" the volunteer was instructed to urinate into the vessel while his penis was touching the inner lid.

As shown below, he typically voided his bladder as per his personal routine in the toilet, and then afterwards used the provided vessel. He reported his results as follow, with SS denoting stainless steel, and cu denoting copper. All voids were made standing. After urination in the vessel, the volunteer emptied the vessel into a scored beaker to measure the volume of evacuated urine. The volume figure is the urine collected in the vessel.

| First Session, Example B | | | |
|---|---|---|---|
| $1^{st}$ go - - - | toilet | 11:30 p.m. | |
| $2^{nd}$ go - - - | SS Cup | 11:40 p.m. | 70 ml |
| $1^{st}$ go - - - | toilet | 1:50 a.m | |
| $2^{nd}$ go - - - | SS Cup | 2:01 a.m. | 85 ml. |
| $3^{rd}$ go - - - | SS Cup | 2:07 a.m. | 50 ml |
| $1^{st}$ go - - - | toilet | 5:03 a.m. | |
| $2^{nd}$ go - - - | SS Cup | 5:13 a.m. | 125 ml |
| $1^{st}$ go - - - | toilet | 7:06 a.m. | |
| $2^{nd}$ go - - - | SS Cup | 7:18 a.m. | 85 ml |
| Day | | | |
| $1^{st}$ go - - - | toilet | 2:45 p.m. | |
| $2^{nd}$ go - - - | SS Cup | 2:53 p.m. | 50 ml |

| Second Session, Example B | | | |
|---|---|---|---|
| $1^{st}$ go | 12:25 | toilet | |
| $2^{nd}$ go | 12:34 | SS Cup | 80 ml |
| $3^{rd}$ go | 12:42 | SS Cup | 50 ml |
| $1^{st}$ go | 2:20 | toilet | |
| $2^{nd}$ go | 2:30 | SS Cup | 115 ml |
| $3^{rd}$ go | 2:44 | SS Cup | 40 ml |
| $1^{st}$ go | 4:25 | toilet | |
| $2^{nd}$ go | 4:36 | SS Cup | 80 ml |
| $3^{rd}$ go | 4:47 | SS Cup | 40 ml |
| $1^{st}$ go | 7:24 | toilet | |
| $2^{nd}$ go | 7:34 | SS Cup | 80 ml |
| $3^{rd}$ go | 7:45 | SS Cup | 35 ml |

| Second Session, Example B | | | |
|---|---|---|---|
| DAY | | | |
| 1st go | 1:00 p.m. | toilet | |
| 2nd go | 1:10 p.m. | SS Cup | 50 ml |
| 3rd go | 1:21 p.m. | SS Cup | 50 ml |

| Third Session, Example B | | | |
|---|---|---|---|
| 1st go - - - | toilet | 11:30 p.m. | |
| 2nd go - - - | toilet | 11:35 p.m. | |
| 3rd go - - - | SS Cup | 11:41 p.m. | 50 ml |
| 1st go - - - | toilet | 1:35 a.m. | |
| 2nd go - - - | toilet | 1:47 a.m. | |
| 3rd go - - - | SS Cup | 1:55 a.m. | 40 ml |
| 1st go - - - | toilet | 3:28 a.m. | |
| 2nd go - - - | toilet | 3:35 a.m. | |
| 3rd go - - - | SS Cup | 3:45 a.m. | 50 ml |
| 1st go - - - | toilet | 5:40 a.m. | |
| 2nd go - - - | toilet | 5:47 a.m. | |
| 3rd go - - - | SS Cup | 5:55 a.m. | 60 ml |
| Day | | | |
| 1st go - - - | toilet | 2:30 p.m. | |
| 2nd go - - - | toilet | 2:40 p.m. | |
| 3rd go - - - | SS Cup | 2:47 p.m. | 80 ml |

| Fourth Session, Example B | | | |
|---|---|---|---|
| 1st go | 11:40 p.m. | toilet | |
| 2nd go | 11:50 p.m. | toilet | |
| 3rd go | 12:05 a.m. | SS Cup | 30 ml |
| 1st go | 2:15 a.m. | toilet | |
| 2nd go | 2:22 a.m. | toilet | |
| 3rd go | 2:30 a.m. | SS Cup | 40 ml |
| 1st go | 4:30 a.m. | toilet | |
| 2nd go | 4:37 a.m. | toilet | |
| 3rd go | 4:44 a.m. | SS Cup | 60 ml |
| 1st go | 6:20 a.m. | toilet | |
| 2nd go | 6:25 a.m. | toilet | |
| 3rd go | 6:30 a.m. | SS Cup | 40 ml |
| Day | | | |
| 1st go | 2:10 p.m. | toilet | |
| 2nd go | 2:15 pm | SS Cup | 110 ml |

| Fifth Session, Example B | | | |
|---|---|---|---|
| 1st go | 12:37 a.m. | toilet | |
| 2nd go | 12:44 a.m. | toilet | |
| 3rd go | 12:54 a.m. | SS Cup | 50 ml |
| 1st go | 3:40 a.m. | toilet | |
| 2nd go | 3:47 a.m. | toilet | |
| 3rd go | 3:55 a.m. | SS Cup | 60 ml |
| 1st go | 6:15 a.m. | toilet | |
| 2nd go | 6:22 a.m. | toilet | |
| 3rd go | 6:33 a.m. | SS Cup | 40 ml |
| Day | | | |
| 1st go | 2:30 p.m. | toilet | |
| 2nd go | 2:37 p.m. | SS Cup | 75 ml |

| Sixth Session, Example B | | | |
|---|---|---|---|
| 1st go | 12:15 a.m. | toilet | |
| 2nd go | 12:25 a.m. | toilet | |
| 3rd go | 12:34 a.m. | SS Cup | 60 ml |
| 1st go | 2:55 a.m. | toilet | |
| 2nd go | 3:05 a.m. | toilet | |
| 3rd go | 3:14 a.m. | SS Cup | 50 ml |
| 1st go | 5:25 a.m. | toilet | |
| 2nd go | 5:34 a.m. | toilet | |
| 3rd go | 5:42 a.m. | SS Cup | 40 ml |
| Day | | | |
| 1st go | 3:05 p.m. | toilet | |
| 2nd go | 3:16 p.m. | SS Cup | 60 ml |

| Seventh Session, Example B | | | |
|---|---|---|---|
| 1st go | 12:10 a.m. | toilet | |
| 2nd go | 12:19 a.m. | toilet | |
| 3rd go | 12:28 a.m. | SS cup | 50 ml |
| 1st go | 3:58 a.m. | toilet | |
| 2nd go | 4:10 a.m. | toilet | |
| 3rd go | 4:18 a.m. | SS Cup | 55 ml |
| 1st go | 6:20 a.m. | toilet | |
| 2nd go | 6:26 a.m. | toilet | |
| 3rd go | 6:36 a.m. | SS Cup | 50 ml |
| Day | | | |
| 1st go | 3:10 p.m. | toilet | |
| 2nd go | 3:20 p.m. | SS Cup | 110 ml |

| Eighth Session, Example B | | | |
|---|---|---|---|
| 1st go | 12:38 a.m. | toilet | |
| 2nd go | 12:45 a.m. | toilet | |
| 3rd go | 12:54 a.m. | Cu Cup | 35 ml |
| 1st go | 2:35 a.m. | toilet | |
| 2nd go | 2:45 a.m. | toilet | |
| 3rd go | 2:54 a.m. | Cu Cup | 50 ml |
| 1st go | 5:32 a.m. | toilet | |
| 2nd go | 5:42 a.m. | toilet | |
| 3rd go | 5:50 a.m. | Cu Cup | 45 ml |
| Day | | | |
| 1st go | 2:25 p.m. | toilet | |
| 2nd go | 2:30 p.m. | Cu Cup | 60 ml |

| Ninth Session, Example B | | | |
|---|---|---|---|
| 1st go | 12:10 a.m. | toilet | |
| 2nd go | 12:20 a.m. | toilet | |
| 3rd go | 12:35 a.m. | Cu Cup | 40 ml |
| 1st go | 3:25 a.m. | toilet | |
| 2nd go | 3:30 a.m. | toilet | |
| 3rd go | 3:37 a.m. | Cu Cup | 55 ml |
| 1st go | 5:55 a.m. | toilet | |
| 2nd go | 6:07 a.m. | toilet | |
| 3rd go | 6:14 a.m. | Cu Cup | 35 ml |
| Day | | | |
| 1st go | 3:50 p.m. | toilet | |
| 2nd go | 4:05 p.m. | Cu cup | 50 ml |

| Tenth Session, Example B | | | |
|---|---|---|---|
| 1st go | 11:30 p.m. | toilet | |
| 2nd go | 12:10 a.m. | toilet | |

-continued

| Tenth Session, Example B | | | |
|---|---|---|---|
| 3$^{rd}$ go | 12:20 a.m. | Cu Cup | 40 ml |
| 1$^{st}$ go | 3:15 a.m. | toilet | |
| 2$^{nd}$ go | 3:22 a.m. | toilet | |
| 3$^{rd}$ go | 3:29 a.m. | Cu Cup | 40 ml |
| 1$^{st}$ go | 5:10 a.m. | toilet | |
| 2$^{nd}$ go | 5:19 a.m. | toilet | |
| 3$^{rd}$ go | 5:30 a.m. | Cu Cup | 50 ml |
| Day | | | |
| 1$^{st}$ go | 4:00 p.m. | toilet | |
| 2$^{nd}$ go | 4:10 p.m. | Cu cup | 60 ml |

| Eleventh Session, Example B | | | |
|---|---|---|---|
| 1$^{st}$ go | toilet | 1:25 a.m. | |
| 2$^{nd}$ go | toilet | 1:32 a.m. | |
| 3$^{rd}$ go | Cu Cup | 1:45 a.m. | 75 ml |
| 1$^{st}$ go | toilet | 6:15 a.m. | |
| 2$^{nd}$ go | toilet | 6:28 a.m. | |
| 3$^{rd}$ go | Cu Cup | 6:44 a.m. | 60 ml |
| Day | | | |
| 1$^{st}$ go | toilet | 4:04 p.m. | |
| 2$^{nd}$ go | Cu cup | 4:12 p.m. | 60 ml |

Some observations are in order concerning the results of Example B. First, the test volunteer reported reduced fluid intake at the time of the switch from the stainless steel vessel to the copper vessel. Accordingly, this experiment was not taken to have bearing on the efficacy of these two materials.

The fact that the test subject was able to reliably expel a substantial amount of urine routinely, even after two conventional voidings in a short period point to retained urine after normal voiding. This retain urine was substantially eliminated through use of the virtual catheter, when we compare the volume of that void to the retain urine volumes described in the literature.

The test subject reported longer intervals between urination using the virtual catheter, and longer sleep intervals: " . . . good uninterrupted sleep."

Example C

In this example, an approximately 80-year old male, with BPH, volunteered to use a a copper vessel supplied to him, and record his results. By "use" the volunteer was instructed to urinate into the vessel while his penis was touching the inner lid.

As shown below, he typically voided his bladder one time routine in the toilet, and then promptly afterwards used the provided vessel (within three minutes). Both voids were made standing. After urination in the vessel, the volunteer emptied the vessel into a scored beaker to measure the volume of evacuated urine. Reports are reported below. The volume figure is the urine collected in the vessel.

| 1. | Toilet | 10:05 | | |
| 2. | Cup | 10:06:30 | 65 ml | 1 1/2 minute interval |
| 1. | toilet | 1:10 a.m. | | |
| 2. | cup | 1:12 a.m. | 70 ml | 2 minute interval |
| 1. | toilet | 3:45 a.m. | | |
| 2. | cup | 3:48 a.m. | 40 ml | 2 1/2 minute interval |
| 1. | toilet | 6:30 a.m. | | |
| 2. | cup | 6:32 a.m. | 60 ml | 2 minute interval |
| 1. | toilet | 10:05 pm | | |

| 2. | Cup | 10:06 pm | 65 ml | 1 1/2 minute interval |
| 1. | toilet | 1:10 a.m. | | |
| 2. | cup | 1:12 a.m. | 70 ml | 2 minute interval |
| 1. | toilet | 3:45 a.m. | | |
| 2. | cup | 3:48 a.m. | 40 ml | 2 1/2 minute interval |
| 1. | toilet | 6:30 a.m. | | |
| 2. | cup | 6:32 a.m. | 60 ml | 2 minute interval |

The user from these tests reported that the device allowed him to shorten his typical interval between successful double voids (DBI). By successful, we mean a void resulting in a substantial amount of urine, i.e. more than 30 ml. When urinating in a toilet, the user reported that additional time was often required for a successful second or double void.

Example D

In this example, an approximately 80-year old male, with BPH, volunteered to use a a copper vessel supplied to him, and record his results. By "use" the volunteer was instructed to urinate into the vessel while his penis was touching the inner lid.

As shown below, he typically voided his bladder one time routine in the toilet (T), and then promptly afterwards used the provided copper vessel (Cu) (within three minutes) a first time, and then a second time within an additional three minutes. All voids were made standing. After urination in the vessel, the volunteer emptied the vessel into a scored beaker to measure the volume of evacuated urine. Reports are reported below. The volume figure is the urine collected in the vessel for each urination.

| 11:25 pm | T | | |
| 11:27 pm | Cu | 110 ml | 3 minutes |
| 11:30 pm | Cu | 30 ml | 2 minutes |
| 3:15 am | T | | |
| 3:18 am | Cu | 70 ml | 3 minutes |
| 3:21 am | Cu | 30 ml | 3 minutes |
| 5:50 am | T | | |
| 5:34 am | Cu | 30 ml | 2 minutes |
| 5:37 am | Cu | 20 ml | 3 minutes |

The test subject noted with great pleasure that he was able to get nearly four hours of sleep (over three and a half hours) between the last evening void and his first void during the night/early morning. The most important issue here is the reduced DVI or 'double voiding interval'. Normally this individual would wait 10 or more minutes between the double void. Sleep studies show the longer sleep is interrupted the more difficult it is to again fall asleep. This advantage was stated by the test subject.

Example E

This example involved an experiment to null out the effect of thermal transfer versus the effect of reduced pressure requirements to urinate. The test subject was an approximately 80 year old male with BPH. The subject performed all urination from a standing position, and recorded all urine volumes by transferring the urine into a scored beaker. The subject was told to urinate ad libitum.

For the first set of test days, the volunteer uses a paper cup, and was instructed to perform all urination standing, and then measure and record volumes. For the second set of test days, the volunteer uses a steel cup, and was instructed to perform all urination standing, and then measure and record volumes.

For this set of experiments, the paper cup—possessing very low thermal conductivity—was intended to capture/demonstrate solely those benefits relating to reduced pressure needed to urinate (as compared to the pressure needed to urinate into the toilet).

For the second set of experiments, the steel cup was intended to show the incremental benefits of (cold) thermal transfer to assist in initiation of urination as compared to the effectively non-thermal conductive paper cup, which offers reduced pressure requirements but not meaningful (cold) thermal transfer.

For both sets of experiments, the subject noted where he urinated during his sleep cycle. The sleep cycle urinations are noted by the italicized times.

Results are presented in the tables below.

| Paper Cup Time (commenced in early evening) | Urine Volume | Time from prior urination/interval |
|---|---|---|
| 6:30 PM | 50 ML | |
| 6:40 PM | 60 ML | 10 min |
| 8:30 PM | 110 ML | 110 min |
| 8:36 PM | 50 ML | 6 min |
| 8:43 PM | 30 ML | 7 min |
| 10:30 PM | 25 ML | 103 min |
| Day One | | |
| *12:10 AM* | 60 ML | 100 min |
| *1:50 AM* | 125 ML | 100 min |
| *1:55 AM* | 25 ML | 5 min |
| *4:25 AM* | 145 ML | 150 min |
| *4:35 AM* | 40 ML | 5 min |
| 7:30 AM | 100 ML | 175 min |
| 7:40 AM | 50 ML | 10 min |
| 10:30 AM | 175 ML | 170 min |
| 11:45 AM | 125 ML | 75 min |
| 11:55 AM | 50 ML | 10 min |
| 2:00 PM | 100 ML | 125 min |
| 4:05 PM | 50 ML | 125 min |
| 7:00 PM | 125 ML | 175 min |
| 9:30 PM | 75 ML | 150 min |
| 9:40 PM | 50 ML | 10 min |
| 11:45 PM | 75 ML | 125 min |
| Day Two | | |
| *2:10 am* | 125 ml | 140 min |
| *2:20 am* | 35 ml | 10 min |
| *3:45 am* | 50 ml | 85 min |
| *6:10 am* | 50 ml | 140 min |
| *6:25 am* | 20 ml | 15 min |
| 8:45 am | 50 ml | 140 min |
| 9:00 am | 20 ml | 15 min |
| 12:20 pm | 80 ml | 200 min |
| 2:35 pm | 75 ml | 175 min |
| 5:00 pm | 100 ml | 145 min |
| 6:30 pm | 75 ml | 90 min |
| *9:00 pm* | 75 ml | 150 min |
| Day Three | | |
| *1:00 AM* | 90 ML | 240 min |
| *1:15 AM* | 50 ML | 15 min |
| *3:35 AM* | 100 ML | 140 min |
| *3:45 AM* | 50 ML | 10 min |
| 8:00 AM | 125 ML | 270 min |
| 10:10 AM | 175 ML | 130 min |
| 12:50 AM | 75 ML | 160 min |
| 5:30 PM | 75 ML | 280 min |
| *9:10 PM* | 100 ML | 220 min |
| *9:17 PM* | 60 ML | 17 min |
| Day Four | | |
| 3:20 AM | 200 ML | 243 min |
| 7:20 AM | 100 ML | 180 min |
| 7:30 AM | 40 ML | 10 min |
| 11:10 AM | 100 ML | 220 min |
| 11:18 AM | 50 ML | 8 min |
| 1:00 PM | 75 ML | 102 min |
| 2:00 PM | 85 ML | 60 min |
| 3:00 PM | 50 ML | 60 min |
| 6:00 PM | 75 ML | 180 min |
| 7:00 PM | 25 ML | 60 min |
| *10:15 PM* | 100 ML | 195 min |
| *11:30 PM* | 80 ML | 75 min |
| *11:37 PM* | 80 ML | 7 min |
| Day Five | | |
| *1:00 AM* | 60 ML | 100 min |
| *5:55 AM* | 150 ML | 295 min |
| *8:30 AM* | 100 ML | 155 min |
| *8:35 AM* | 75 ML | 5 min |
| 10:05 AM | 40 ML | 90 min |
| 11:30 AM | 25 ML | 90 min |
| 2:15 pm | 85 ML | 165 min |
| 2:20 pm | 10 ML | 5 min |
| *9:20 pm* | 100 ML | 300 min |
| *9:30 pm* | 80 ML | 10 min |
| *10:30 pm* | 50 ML | 60 min |
| Day Six | | |
| *2:00 am* | 100 ML | 210 min |
| *5:05 am* | 150 ML | 185 min |
| *5:20 am* | 70 ML | 15 min |
| *7:15 am* | 50 ML | 115 min |
| 8:30 am | 25 ML | 75 min |
| 11:35 am | 75 ML | 185 min |
| 1:00 pm | 60 ML | 95 min |
| 5:30 pm | 125 ML | 270 min |
| *8:45 pm* | 125 ML | 195 min |
| *9:30 pm* | 125 ML | 45 min |
| *9:45 pm* | 75 ML | 15 min |
| Day Seven | | |
| *12:25 am* | 80 ML | 150 |
| *1:50 am* | 0 ML (failure) | 85 |
| *2:00 am* | 75 ML | 10 min |
| *6:00 am* | 175 ML | 240 min |
| 9:55 am | 200 ML | 235 min |
| 1:00 pm | 100 ML | 175 min |
| 1:15 pm | 75 ML | 15 min |
| 2:15 pm | 100 ML | 60 min |
| 3:20 pm | 50 ML | 65 min |
| 4:45 pm | 50 ML | 85 min |
| 8:20 pm | 150 ML | — |
| 10:40 pm | 100 ML | 140 min |
| *10:50 pm* | 100 ML | 10 min |
| Day Eight | | |
| *1:00 am* | 125 ML | 130 min |
| *1:10 am* | 75 ML | 10 min |
| *3:30 am* | 100 ML | 140 min |
| *5:30 am* | 75 ML | 120 min |
| *5:45 am* | 75 ML | 15 min |
| 9:30 am | 100 ML | 225 min |
| 9:40 am | 50 ML | 10 min |
| 10:25 am | 50 ML | 45 min |
| 12:30 am | 50 ML | 125 min |
| 2:15 pm | 75 ML | 105 min |
| 3:30 pm | 50 ML | 75 min |
| 7:00 pm | 100 ML | 210 min |
| 7:20 pm | 75 ML | 20 min |
| *9:40 pm* | 75 ML | 140 min |
| Day Nine | | |
| *12:35 am* | 125 ML | 175 min |
| *1:20 am* | 60 ML | 45 min |
| *2:50 am* | 100 ML | 90 min |
| *6:20 am* | 125 ML | 210 min |
| 8:15 am | 40 ML | 115 min |
| 8:30 am | 50 ML | 15 min |
| 11:30 am | 100 ML | 180 min |
| 12:35 pm | 50 ML | 65 min |
| 3:05 pm | 40 ML | 210 min |
| 5:25 pm | 100 ML | 140 min |
| 7:20 pm | 100 ML | 115 min |
| 7:30 pm | 25 ML | 10 min |

-continued

| Time | Urine Volume | Time from prior urination/interval |
|---|---|---|
| 9:30 pm | 125 ML | 120 min |
| 11:05 pm | 130 ML | 95 min |
| *Day Ten* | | |
| 2:35 am | 125 ML | 210 min |
| 2:40 am | 60 ML | 5 min |
| 4:30 am | 100 ML | 110 min |
| 7:00 am | 90 ML | 150 min |
| 10:00 am | 110 ML | 180 min |
| 10:10 am | 40 ML | 10 min |
| 1:45 pm | 100 ML | 210 min |
| 3:15 pm | 40 ML | 90 min |
| 7:40 pm | 150 ML | 265 min |
| 7:50 pm | 15 ML | 10 min |
| 10:45 pm | 25 ML | 175 min |
| 10:55 pm | 10 ML | 10 min |
| *Day Eleven* | | |
| 12:30 am | 25 ML | 95 min |
| 12:40 am | 10 ML | 10 min |
| 6:50 am | 135 ML | 250 min |
| 7:00 am | 25 ML | 10 min |
| 1:20 pm | 175 ML | 420 min |
| 5:00 pm | 110 ML | 220 min |
| 5:15 pm | 75 ML | 15 min |
| 7:00 pm | 100 ML | 105 min |
| 9:45 pm | 50 ML | 125 min |
| 9:50 pm | 50 ML | 5 min |
| *Day Twelve* | | |
| 1:00 am | 175 ML | 235 min |
| 2:45 am | 125 ML | 90 min |
| 3:00 am | 40 ML | 15 min |
| 5:20 am | 70 ML | 140 min |
| 5:30 am | 40 ML | 10 min |
| 8:30 am | 80 ML | 180 min |
| 8:40 am | 75 ML | 10 min |

| Steel Cup Trial Time | Urine Volume | Time from prior urination/interval |
|---|---|---|
| 10:50 pm | 60 ML | n/a |
| 10:55 pm | 30 ML | 5 min |
| *First full Day - Day One* | | |
| 1:40 am | 100 ml | 225 min |
| 1:45 am | 59 ml | 5 min |
| 7:05 am | 125 ml | 200 min |
| 7:11 am | 75 ml | 6 min |
| 12:00 am | 150 ml | 289 min |
| 12:07 am | 100 ml | 7 min |
| 1:50 pm | 75 ml | 103 min |
| 3:20 pm | 85 ml | 90 min |
| 5:30 pm | 75 ml | 140 min |
| 5:35 pm | 60 ml | 5 min |
| 11:00 pm | 175 ml | 325 min |
| 11:06 pm | 75 ml | 6 min |
| *Day Two* | | |
| 2:00 am | 100 ml | 174 min |
| 2:06 am | 75 ml | 6 min |
| 6:05 am | 150 ml | 239 min |
| 6:10 am | 75 ml | 5 min |
| 8:15 am | 125 ml | 125 min |
| 8:22 am | 80 ml | 7 min |
| 10:20 am | 90 ml | 118 min |
| 10:50 am | 75 ml | 30 min |
| 2:45 pm | 75 ml | 235 min |
| 5:00 pm | 80 ml | 140 min |
| 8:30 pm | 75 ml | 210 min |
| *Day Three* | | |
| 12:40 am | 130 ml | 250 min |
| 12:44 am | 40 ml | 4 min |
| 2:30 am | 80 ml | 116 min |
| 2:35 am | 50 ml | 5 min |
| 5:50 am | 100 ml | 195 min |
| 6:00 am | 30 ml | 10 min |
| 12:00 noon | 175 ml | 360 min |
| 12:10 pm | 100 ml | 10 min |
| 3:35 pm | 125 ml | 205 min |
| 3:42 pm | 60 mil | 7 min |
| 9:10 pm | 125 ml | 328 min |
| 11:30 pm | 75 ml | 140 min |
| 11:36 pm | 100 ml | 6 min |
| *Day Four* | | |
| 3:15 am | 100 ml | 219 min |
| 3:21 am | 90 ml | 6 min |
| 5:30 am | 125 ml | 129 min |
| 5:35 am | 60 ml | 5 min |
| 9:10 am | 100 ml | 220 min |
| 9:16 am | 50 ml | 6 min |
| 1:15 pm | 110 ml | 239 min |
| 4:00 pm | 140 ml | 225 min |
| 7:55 pm | 110 ml | 235 min |
| 8:00 pm | 30 ml | 5 min |
| 11:20 pm | 105 ml | 200 min |
| 11:27 pm | 75 ml | 7 min |
| *Day Five* | | |
| 1:34 am | 135 ml | 127 min |
| 1:38 am | 75 ml | 4 min |
| 3:38 am | 150 ml | 120 min |
| 3:45 am | 75 ml | 7 min |
| 7:00 am | 100 ml | 210 min |
| 7:08 am | 105 ml | 8 min |
| 9:00 am | 100 ml | 112 min |
| 9:05 am | 80 ml | 5 min |
| 9:15 am | 75 ml | 10 min |
| 1:00 pm | 150 ml | 225 min |
| 4:20 pm | 150 ml | 190 min |
| 4:28 pm | 110 ml | 8 min |
| 8:20 pm | 90 ml | 232 min |
| 10:50 pm | 60 ml | 150 ml |
| *Day Six* | | |
| 2:45 am | 60 ml | 235 min |
| 2:55 am | 50 ml | 10 min |
| 7:55 am | 115 ml | 240 min |
| 8:01 am | 50 ml | 6 min |

Quantitative analysis is provided below

| Day | # of urinations (full 24 hour period) | Avg Time Interval between voids sessions (net of secondary/tertiary voids, i.e. interval starts 15 min or less from completion of void session, includes time from prior day where applicable) | # of voids less than 50 ML | # of double voids (secondary or tertiary voids in 15 min interval or less) | Longest Interval between urination (over 24 hour period) |
|---|---|---|---|---|---|
| Paper Day One | 16 | 133 min | 2 | 5 | 175 min |
| Paper - Day Two | 12 | 141 min | 3 | 3 | 200 min |

| Day | # of urinations (full 24 hour period) | Avg Time Interval between voids sessions (net of secondary/tertiary voids, i.e. interval starts 15 min or less from completion of void session, includes time from prior day where applicable) | # of voids less than 50 ML | # of double voids (secondary or tertiary voids in 15 min interval or less) | Longest Interval between urination (over 24 hour period) |
|---|---|---|---|---|---|
| Paper - Day Three | 10 | 182 min | 0 | 2 | 175 min |
| Paper - Day Four | 13 | 137.5 min | 2 | 3 | 200 min |
| Paper - Day Five | 11 | 144.3 min | 3 | 3 | 295 min |
| Paper - Day Six | 11 | 152.7 min | 1 | 2 | 270 min |
| Paper Day Seven | 13 | 156 min | 1 | 3 | 240 min |
| Paper - Day Eight | 14 | 121.4 min | 0 | 3 | 225 min |
| Paper - Day Nine | 14 | 130 min | 3 | 3 | 210 min |
| Paper - Day Ten | 12 | 173.8 | 5 | 4 | 265 min |
| Paper - Day Eleven | 10 | 165.8 | 3 | 4 | 420 min |
| | Paper Avg urinations per 24 hr 12.3/day | | Paper - avg #voids less than 50 ML 2.1/day | Paper - # of double voids (secondary or tertiary voids in 15 min interval or less) 3.2/day | 243.2 min - avg longest-daily interval |
| Steel Day one | 12 | | 0 | 5 | 325 min |
| Steel Day two | 11 | | 0 | 3 | 239 min |
| Steel Day three | 13 | | 2 | 6 | 328 min |
| Steel Day four | 12 | | 1 | 5 | 239 min |
| Steel Day five | 14 | | 0 | 6 | 232 min |
| | Steel Avg Urinations per 24 hr 12.4/day | | Steel - avg #voids less than 50 ML 0.6/day | Steel - # of double voids (secondary or tertiary voids in 15 min interval or less) 5/day | 272.6 min - avg longest daily interval |

The text table analyzes the sleep hours record in bolded italics in the tables.

| Sleep Cycle | # of nocturia (all voids) | Avg sleep interval (excluding double/tertiary voids - voids within 15 minutes) | Longest Interval between urination (over sleep cycle) |
|---|---|---|---|
| Paper Sleep Cycle #1 | 7 | 131.25 | 175 min |
| Paper Sleep Cycle #2 | 8 | 128 | 150 min |
| Paper Sleep Cycle #3 | 6 | 216.7 | 270 min |
| Paper Sleep Cycle #4 | 5 | 165 | 243 min |
| Paper Sleep Cycle #5 | 7 | 164 | 295 min |
| Paper Sleep Cycle #6 | 7 | 174 | 300 min |
| Paper Sleep Cycle #7 | 6 | 130 | 240 min |
| Paper Sleep Cycle #8 | 7 | 132.5 | 140 min |
| Paper Sleep Cycle #9 | 5 | 129.1 | 210 min |
| Paper Sleep Cycle #10 | 5 | 141.3 | 210 min |
| Paper Sleep Cycle #11 | 6 | 173.3 | 250 min |
| Paper Sleep Cycle #12 | 9 | 153 | 235 min |
| | Paper avg # of nocturia (all voids) 6.7 | Paper Avg sleep interval (excluding double/tertiary voids - voids within 15 minutes) 167.1 min | Paper Avg Longest Interval between urination (over sleep cycle) 247.1 min |
| Steel Sleep Cycle # 1 | 6 | 212.5 | 225 min |
| Steel Sleep Cycle # 2 | 6 | 246 | 325 min |
| Steel Sleep Cycle # 3 | 6 | 187 | 250 min |
| Steel Sleep Cycle # 4 | 6 | 162.7 | 219 min |
| Steel Sleep Cycle # 5 | 8 | 164.3 | 210 min |
| Steel Sleep Cycle # 6 | 5 | 208.3 | 240 min |
| | Steel avg # of nocturia (all voids) 6.2 | Steel Avg sleep interval (excluding double/tertiary voids - voids within 15 minutes) 196.8 min | Steel Avg Longest Interval between urination (over sleep cycle) 244.8 |

What is claimed is:

1. A device configured to facilitate urination by a male, comprising a vessel having a contact surface area at and adjacent a top edge of the vessel configured to be placed in contact with the penis, the vessel being capable of collecting urine, wherein the contact surface area comprises a thermally conductive material having a thermal conductivity of greater than 20 watts per meter-kelvin, and wherein the vessel is configured to initiate and continue urination by a male.

2. The device according to claim 1, where the device has a protrusion extending outwardly from an outer wall of the vessel, with the protrusion having a contact surface area configured to contact the scrotum of the male.

3. The device according to claim 2, wherein the contact surface area of the protrusion comprises a thermally conductive material having a thermal conductivity of at least 20 watts per meter-kelvin.

4. The device according to claim 1, wherein the vessel comprises an antimicrobial coating on its surfaces.

5. A method for reducing the frequency of nocturia for a male, comprising contacting the penis of the male with the contact surface area of the device according to claim 1 and urinating while the penis is in contact with the contact surface area.

6. A method for extending the longest daily interval between urinations for a male, comprising contacting the penis of the male with the contact surface area of the device according to claim 1 and urinating while the penis is in contact with the contact surface area.

7. A method for increasing the average duration of sleep for a male, comprising contacting the penis of the male with the contact surface area of the device according to claim 1 and urinating while the penis is in contact with the contact surface area.

8. A method for reducing the number of daily incontinence episodes in a male, comprising contacting the penis of the male with the contact surface area of the device according to claim 1 and urinating while the penis is in contact with the contact surface area.

9. A method for assisting initiating of urination in a male with pelvic floor hyperactivity comprising contacting the penis of the male with contact surface area of the device according to claim 1 and urinating while the penis is in contact with the contact surface area.

10. A method for reducing IPSS survey scores of a group of male users versus male non-users, comprising contacting the penis of each male user with contact surface area of the device according to claim 1 and urinating while the penis is in contact with the contact surface area.

11. The device according to claim 1, wherein the thermally conductive material has a thermal conductivity of greater than 100 watts per meter-kelvin.

12. The device according to claim 1, wherein the contact surface area is at least 0.5 square inches.

13. The device according to claim 1, wherein the contact surface area is at least 1 square inch.

14. A method of reducing urinary retention in a male having benign prostatic hyperplasia, comprising contacting the penis of the male having benign prostatic hyperplasia with a contact surface area of a device and urinating while the male is in a standing position with the penis in contact with the contact surface area, wherein the contact surface area is at least 0.5 square inches and comprises a thermally conductive material and is at an initial temperature at least 14° F. lower than a temperature of the penis.

15. The method according to claim 14, wherein the device comprises a vessel having the contact surface area at and adjacent a top edge of the vessel, the vessel being capable of collecting urine, wherein the contact surface area has a shape configured to initiate and continue urination by the male having benign prostatic hyperplasia.

16. The method according to claim 15, wherein the thermally conductive material has a thermal conductivity of greater than 20 watts per meter-kelvin.

17. The method according to claim 16, wherein the contact surface area of the vessel slopes inwardly from the top edge of the vessel toward the bottom of the vessel.

18. The method according to claim 17, wherein, when the top edge of the vessel is horizontal, the contact surface area of the vessel is at an angle of less than 40° to vertical.

19. The method according to claim 15, wherein the contact surface area is at least 1 square inch.

20. The method according to claim 15, wherein the contact surface area has an angled, curved or concave shape to increase contact with the penis.

21. The method according to claim 15, wherein the top edge of the vessel has an hourglass shape comprising two wider portions forming openings separated by a narrower portion.

22. The method according to claim 15, wherein the contact surface area comprises metal.

23. The method according to claim 15, wherein the vessel includes markings to show volume.

24. The method according to claim 15, wherein the vessel comprises an antimicrobial coating on its surfaces.

25. The method according to claim 15, wherein the contact surface area comprises a thermally conductive material having a thermal conductivity of at least 100 watts per meter-kelvin.

26. The method according to claim 15, wherein at least some portions other than the contact surface area comprise a material having a thermal conductivity less than that of the contact surface area.

27. The method according to claim 15, further comprising treating the male with a drug therapy selected from the group of alpha blockers, 5α-reductase inhibitors and phosphodiesterase type 5 inhibitors.

28. The method of claim 15, further comprising at least one additional urination prior to urinating while the male is in a standing position with the penis in contact with the contact surface area, wherein a void interval between urinations is less than five minutes.

29. The method of claim 15, further comprising at least one additional urination prior to urinating while the male is in a standing position with the penis in contact with the contact surface area, wherein a void interval between urinations is less than ten minutes, and the retained urine in the bladder is reduced at least 20% for a given patient population.

30. The method of claim 15, wherein the contact surface area comprises a thermally conductive material having a thermal conductivity of at least 100 watts per meter-kelvin.

31. A device configured to facilitate urination by a male, comprising a vessel having an opening at a top edge of the vessel and a bottom portion capable of collecting urine from a complete emptying of the male's bladder, wherein the bottom portion and the opening are connected to form one contiguous, undivided space, the vessel having a contact surface area at and adjacent a top edge of the vessel configured to be placed in contact with the penis, wherein the contact surface area comprises a thermally conductive material and is configured to initiate and continue urination by a male.

32. The device of claim 31, wherein the contact surface area comprises a thermally conductive material having a thermal conductivity of at least 20 watts per meter-kelvin.

33. The device of claim 31, wherein the contact surface area comprises a thermally conductive material having a thermal conductivity of at least 100 watts per meter-kelvin.

34. The device according to claim 31, wherein the contact surface area is at least 0.5 square inches.

35. The device according to claim 31, wherein the contact surface area is at least 1 square inch.

36. The device according to claim 31, wherein the vessel further comprises at least one external handle.

* * * * *